(12) United States Patent
Leyns et al.

(10) Patent No.: US 9,074,989 B2
(45) Date of Patent: Jul. 7, 2015

(54) SCREENING DEVICE FOR SCREENING PLANT SPECIMENS

(75) Inventors: Frederik Leyns, Oosterzele (BE); Cádrick Vandaele, Wortegem-Petegem (BE); Pierre Lejeune, Tilff (BE); Jeroen Baert, Erpe-Mere (BE); Fabio Fiorani, Jülich (DE)

(73) Assignee: BASF Plant Science Company GmbH, Ludwigshafen (DE)

( * ) Notice: Subject to any disclaimer, the term of this patent is extended or adjusted under 35 U.S.C. 154(b) by 0 days.

(21) Appl. No.: 14/129,449

(22) PCT Filed: Jun. 25, 2012

(86) PCT No.: PCT/IB2012/053194
§ 371 (c)(1),
(2), (4) Date: Dec. 26, 2013

(87) PCT Pub. No.: WO2013/001436
PCT Pub. Date: Jan. 3, 2013

(65) Prior Publication Data
US 2014/0154729 A1    Jun. 5, 2014

Related U.S. Application Data

(60) Provisional application No. 61/501,297, filed on Jun. 27, 2011.

(30) Foreign Application Priority Data

Jun. 27, 2011  (EP) .................................. 11171568

(51) Int. Cl.
G01N 21/17   (2006.01)
A01G 7/00    (2006.01)
G01N 21/84   (2006.01)

(52) U.S. Cl.
CPC  *G01N 21/17* (2013.01); *A01G 7/00* (2013.01); *G01N 21/84* (2013.01)

(58) Field of Classification Search
CPC ...................................................... G01N 21/84
USPC ...................................................... 250/458.1
See application file for complete search history.

(56) References Cited

U.S. PATENT DOCUMENTS 5,130,545 A       7/1992  Lussier
2004/0263957 A1  12/2004  Hirahara et al.
(Continued)

FOREIGN PATENT DOCUMENTS

DE    197 16 468 A1    10/1998
DE    199 60 044 A1     6/2001
(Continued)

OTHER PUBLICATIONS

International Search Report for PCT/IB2012/053194 mailed Nov. 15, 2012.

*Primary Examiner* — Kiho Kim
(74) *Attorney, Agent, or Firm* — Drinker Biddle & Reath LLP

(57) ABSTRACT

A screening device (110) for screening at least one plant specimen (112) in a plurality of plant specimens (114) is disclosed. The screening device (110) comprises a detector (116) adapted for acquiring spatially resolved images (117). The screening device (110) further comprises at least one selection device (118) adapted for selecting a single plant specimen (120) or a group of plant specimens (122) from the plurality of plant specimens (114) for imaging by the detector (116). The selection device (118) comprises a deflection device (124) adapted for deflecting electromagnetic waves propagating between the plant specimens (112) and the detector (116).

24 Claims, 2 Drawing Sheets

(56) References Cited

U.S. PATENT DOCUMENTS

Figure 1A:
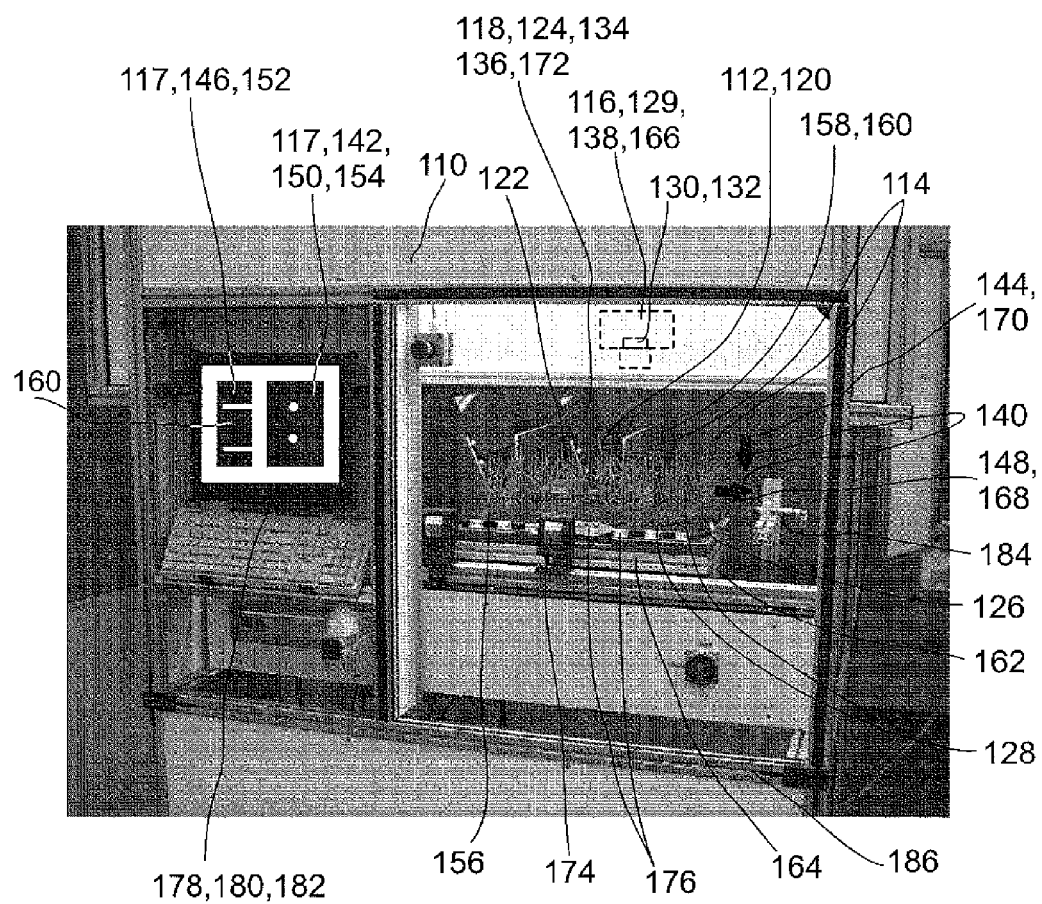

| | | |
|---|---|---|
| 2011/0116688 A1 | 5/2011 | Li et al. |
| 2011/0167721 A1* | 7/2011 | Lejeune et al. .................. 47/65 |

FOREIGN PATENT DOCUMENTS

| | | |
|---|---|---|
| DE | 10 2005 050 302 A1 | 4/2007 |
| EP | 1 443 377 A2 | 8/2004 |
| TW | 201116799 A1 | 5/2011 |
| WO | WO-93/13491 A1 | 7/1993 |
| WO | WO-2004/068934 A2 | 8/2004 |
| WO | WO-2006/029987 A1 | 3/2006 |
| WO | WO-2007/045199 A1 | 4/2007 |
| WO | WO-2007/093444 A1 | 8/2007 |
| WO | WO-2010/031780 A1 | 3/2010 |

\* cited by examiner

SCREENING DEVICE FOR SCREENING PLANT SPECIMENS

RELATED APPLICATIONS

This application is a national stage application (under 35 U.S.C. §371) of PCT/IB2012/053194, filed Jun. 25, 2012, which claims benefit of U.S. Provisional Application No. 61/501,297, filed Jun. 27, 2011, and European Application No. 11171568.6, filed Jun. 27, 2011.

FIELD OF THE INVENTION

The invention relates to a screening device and a method for screening at least one plant specimen in a plurality of plant specimens. The invention further relates to a tracking method for tracking growth conditions of a plurality of plant specimens, use of the screening device in a method for improved growing of plant specimens, a method for phenotyping, for selecting the most desired genotypes based on phenotype scoring, and to a method for rapid analysis of stress resistance of growing plant specimens.

Devices and methods of this kind may be applied in all fields of agricultural research and manufacturing and in all fields of chemical and/or biological technology related to plants and plant specimens. Preferably, the device and methods according to the present invention may be applied to the technical field of testing of plants and testing of methods for treatment of plants, such as one or more of: testing and/or evaluation of optimum growth conditions; testing of resistance of plants against specific types of stress; testing of specific fertilizers and/or nutrients; the selection and/or breeding of plants having one or more desired properties; the testing of the effect and/or effectiveness of specific treatments, such as treatments of the plants or plant specimens with fertilizers and/or pesticides. However, other applications of the present invention are possible.

RELATED ART

As a general practice in several agricultural and horticultural applications, plant cultivation is initiated by sowing seeds in high density arrays, preferably rows, arranged e.g. in dedicated plastic trays or containers with soil or an inert substrate or a liquid nutrient solution formulation. At a given time after germination suitable seedlings may be selected for transplantation onto their destination containers.

In automated systems this selection is efficiently done by means of camera systems. If the plant shape allows top view distinction between healthy and unhealthy plantlets, or between plantlets characterized by contrasting morphological features, state of the art camera systems may be used. WO 2004/068934 A2 discloses a process for breeding plants, comprising growing plants of a species in an array of containers charged with growing medium of uniform characteristics in an environment of controlled climatic conditions with controlled supply of nutrients and feed water. The process further comprises a changing of the positions of the containers within the environment as required to insure at least substantially uniform exposure of all plants in the containers to conditions in the environment. The process further comprises the step of selecting plants for further breeding for commercial use by comparing the phenotypic characteristics of the plants.

Similarly, EP 1 433 377 A1 discloses an apparatus suitable for use in conjunction with a container in which one or more plants are growing and having associated with it a device for receiving an enquiry signal and automatically responding by transmitting a unique identifier signal. The apparatus comprises transporter means by which a container may be supported for moving the container, means for transmitting the enquiry signal, means for recording the identifier signal as a digital output and computer means to which the digital output is supplied for storage of the data in prescribed format in a database for manipulation to afford comparison of data related to the container. As a preferred apparatus, an imaging device is disclosed which comprises two digital cameras disposed one above another and focused on a position occupied by a plant delivered to a rotatable work support in a form of a circular. Parts containing plants to be imaged may be delivered to a belt conveyor and transferred one by one to a belt conveyor by operation of a picking device. The picking device is operated to push the pot and its plant from the belt conveyor onto the circular plate and the plate rotates through 360 degrees.

Further, WO 2006/029987 A1 provides a method comprising growing a plant in a substantially transparent container charged with a particulate, non-transparent growing medium; and evaluating plant roots through said transparent container by digital imaging. An apparatus for evaluating plant roots in a high throughput manner is also provided. An illustrative apparatus comprises a camera placed below a water-basin recording pictures of the bottom surface of pots.

Similarly, WO 2007/093444 A1 discloses a method and an apparatus to determine the start of flowering in plants. More specifically, the invention concerns a method for determining the start of flowering on an individual plant basis by measuring the reproductive structures of plants from digital images of these structures and deducing the start of flowering from the measurements and average growth rates. The invention also concerns apparatus for determining the start of flowering in plants, particularly in a high-throughput manner.

In WO 2010/031780 A1, an invention is published which relates generally to an improved plant breeding system. More particularly, this invention relates to a method for automated, high throughput analysis of plant phenotype and plant genotype in a breeding program. The invention discloses a method comprising imaging one or more characteristics of the plant while the plant is being moved through an imaging system. The imaging system comprises one or more high speed and/or high resolution cameras.

A critical aspect of plant imaging systems of related art is the ability to turn the plant to capture images from several different angles. Systems exist which turn plants around on a fixed turntable while being photographed, some systems provide several cameras for photographing plants at different angles. Methods for turning plants during imaging and imaging systems comprising one or more high speed and/or high resolution cameras are known.

DE 199 60 044 A1 discloses an inspection device with a camera having a high focal length for generating an image of an object consisting of nearly parallel rays. The inspection device comprises at least one deflection device. In the inspection device, several systems consisting of video cameras with adequate deflection devices may be arranged, with differing directions of view.

In WO 2010/031780 A1 a method for analyzing the impact of genetic modifications on plants and selecting a plant with a genetic modification of interest is published. The method comprises providing a plurality of plants growing under controlled environmental conditions. It also comprises analyzing images for one or more characteristic of the plant. The one or more characteristic may comprise one or more of an observable physical manifestation of the plant, e.g. water use, or effects of disease, pests, and/or stress.

Further, WO 2006/029987 A1 discloses an apparatus for evaluating plant roots. Several plants, or each plant, may carry a unique identifier allowing information concerning those individual plants to be linked to their unique identifier in a computer. Preferably, the identifier is a transponder.

WO 93/13491 A1 provides a process and an arrangement for optical quality control and/or classification of plants. An electronic color camera takes a picture of a plant from above and an electronic half-tone camera takes a picture of the plant from the side. In order to prevent mutual impairment of the images and their evaluation, each camera is preferably so constructed that it is sensitive to light from a light source allocated to the other one and/or by causing a control circuit to switch the two light sources on alternately and trigger the pictures taken of the plant by each camera at a time at which only the light source allocated to the camera is switched on.

In DE 10 2005 050 302 A1 a method and a device for determining, in a contact-free manner, the current nutritional state of a plant and for processing said information in relation to fertilizer recommendations is published. At least one digital image from one part of the plant is captured by means of an image capturing system. The image capturing system comprises a conventional digital camera whereon a bracket is secured, which supports at least one small reference surface which can be displayed on the edge of the image, and a computer is provided as an image evaluation system which is connected to the digital camera in order to transfer the images.

U.S. Pat. No. 5,130,545 A discloses a video imaging plant management system which provides a light source to a plant being analyzed, detects infrared fluorescence emissions from the plant under the light, resolves the plant fluorescence emission over time, and calculates the fluorescence emission decay time from peak to steady state values to provide data indicative of the plant health.

Problem to be Solved

It is therefore an object of the present invention to provide a device and methods which at least partially avoid the disadvantages and shortcomings of the systems and methods known from the prior art. Specifically, it is an object of the present invention to provide a device and methods which enable monitoring and screening grass-like seedlings, which often only contain one fine leaf. Taking pictures from above does not really make sense as one would only get a small spot without information on the length, width, color or curling of the leaf. It is therefore a further objective of the present invention to provide a device and methods for screening plants, especially grass-like plants, cultivated in high-density growth. As in grass-like plants, seedlings being thin erect objects, top views are not useful for this kind of plant specimens, because only a very small part of the object is visible. The present invention developed an imaging system, where even grass-like seedlings can be monitored, screened and/or selected from high-density arrays.

SUMMARY OF THE PRESENT INVENTION

This problem is solved by the device and the methods as claimed in the independent claims. Preferred embodiments of the invention which may be realized in an isolated way or in arbitrary combination, are disclosed in the dependent claims.

In a first aspect of the present invention, a screening device for screening at least one plant specimen in a plurality of plant specimens is disclosed. The screening device may be a single apparatus or may comprise a number of two or more apparatuses, which may be arranged in a centralized or de-centralized way. In case the screening device comprises more than one apparatus, the apparatuses may at least partially be interconnected by mechanical and/or electronical means or may at least partially function in an isolated way.

As used in the present specification, the term comprising or grammatical variations thereof, such as the term comprise, are to be taken to specify the presence of stated features, integers, steps or components or groups thereof, but do not preclude the presence or addition of one or more other features, integers, steps, components or groups thereof. The same applies to the term having or grammatical variations thereof, which is used as a synonym to the term comprising.

The term plant specimen may comprise complete plants or parts of plants, like leaves. It furthermore may comprise plants or parts of plants in different growing states, preferably plant specimen may stand for a seedling, preferably for monocots, e.g. for rice that would be from 0-2 weeks after seeding or for grass. The screening device comprises one or more detectors adapted for acquiring spatially resolved images. In a preferred embodiment, the screening device, which may also be referred to as a screening system, comprises precisely one detector adapted for acquiring the spatially resolved images. However, screening systems comprising more than one detector are generally feasible. Preferably, the detector is designed as a top-view detector, the top-view detector being adapted for viewing the plant specimen and/or the plurality of plant specimens and/or a group of plant specimens from above, e.g. with an essentially vertical viewing direction or viewing axis, such as a viewing direction or viewing axis deviating from a vertical direction by no more than 20°, preferably by no more than 10°, more preferably by no more than 5° or even running exactly in a vertical direction.

The term image, as used in the present invention, may imply any type of images, preferably two-dimensional images. The images may be optical images. The images may comprise transmission images and/or shadow images and/or reflection images. The images may be generated by detecting an emission signal, e.g. a fluorescence and/or phosphorescence signal. Thus, the images may be generated by chlorophyll fluorescence measurements and/or selectable marker fluorescence measurements. The signal which may be used to generate an image may be discrete in time or may be a continuous signal. Other types of images are possible.

The screening device further comprises one or more selection devices adapted for selecting a single plant specimen or a group of plant specimens from the plurality of plant specimens for imaging by the detector. Preferably, the screening device comprises precisely one selection device. However, screening devices having more than one selection device are generally feasible. The term selecting a single plant specimen or a group of plant specimens may imply a simple focusing on a single plant specimen or a group of plant specimens from the plurality of plant specimens. The selection device comprises one or more deflection devices adapted for deflecting electromagnetic waves propagating between the plant specimens and the detector. Preferably, the selection device comprises precisely one deflection device, e.g. one single mirror. However, other embodiments including more than one deflection device are generally feasible, such as embodiments including a plurality of mirrors. As outlined above, the deflection device preferably is designed for supporting a top-view detector. Thus, preferably, the deflection device is adapted for deflecting electromagnetic waves, such as light, travelling in an essentially horizontal direction into an essentially vertical direction or vice versa. Therein, with regard to the term "essentially", reference may be made to the definition above, such that deviations from the horizontal direction or the vertical direction, respectively, by no more than 20° are still tolerable, preferably deviations by no more than 10° or, even more preferably, deviations by no more than 5° or, most preferably, no deviations at all.

Preferably, the selection device, preferably by an appropriate design and/or orientation of the deflection device, is adapted to create a side view of the plant specimen, the group of plant specimen or the plurality of plant specimen. This embodiment may be realized by implementing the option feature discussed above, i.e. the feature of the deflection device being adapted for deflecting electromagnetic waves travelling in an essentially horizontal direction into an essentially vertical direction or vice versa. Thus, the selection device preferably may be designed as a side-view device generating a side view of a selected plant specimen or a selected group of plant specimens, wherein the deflection device is adapted to allow for acquiring the side view by the detector which, preferably, is designed as a top-view detector. Thus, the detector and the selection device may, in combination, be adapted such that spatially resolved images of a side view of the selected plant specimen or the selected group of plant specimens may be acquired by using the top-view detector. The latter implies several advantages in daily practice of plant screening. Thus, specifically in high-throughput screening systems, the use of a top-view detector for generating both side views and/or top views of the plant specimens lowers the design restrictions regarding a motion system and/or of the arrangement of the plant specimens in the plurality of the plant specimens. Thus, even two-dimensional arrangements of plant specimens may be screened, even at a high density of the plant specimens, by avoiding the problem of a collision or direct contact of the detector and the plant specimens. Still, side view images of the plant specimens arranged in a two-dimensional arrangement may be acquired, providing valuable screening information, as opposed to a top view arrangement.

The term deflecting electromagnetic waves may comprise a reflecting of electromagnetic waves and/or a change of the propagation direction of the electromagnetic waves, especially of the wave fronts of the electromagnetic waves.

The term electromagnetic waves may comprise light in the visible range, infrared and near-infrared light. It may comprise monochromatic light as well as a broad spectrum of light and it may comprise incoherent light as well as coherent light. Other types of electromagnetic waves are also possible.

The screening device further may comprise at least one plant container containing a plurality of plant specimens or a plurality of plant containers containing at least one plant specimen, preferably the plant specimens growing in rows.

The term plant container, as used in the present invention, may imply any type of container which is suited to at least partially hold a growing medium and/or a plant or a plant specimen, such as by providing a mechanical support and/or a casing, which fully or partially surrounds the growing medium and/or the plant or plant specimen. The plant containers may be of arbitrary shape and may be selected from the group containing pots, bowls, cups, trays or any other shape. Basically, the plant containers may at least partially surround a growing medium or may even be part of the growing medium itself. Thus, the growing medium at least partially may be solidified, in order to provide a mechanical protection and in order to prevent from disintegrating. Thus, the plant container may comprise an outer layer of the growing medium, which is solidified, whereas a further part of the growing medium is at least partially comprised in this outer layer. Preferably, a plant container may be cut into several areas. The different areas may be connected, e.g. fluidly connected, or may be completely separated. Preferably, the plant specimens may grow in rows. The term rows may comprise high-density arrays. Each plant container may comprise at least one row of plant specimens. The row of plant specimens may essentially be perpendicular or parallel to a transport direction of a motion system for providing a relative motion between the plant containers and the detector. The plant container may contain at least one growing medium, e.g. a soil, an inert substrate, a transparent substrate, preferably earth or a liquid nutrient solution formulation. Each plant container may comprise at least one growing medium and at least one plant specimen, preferably a plurality of plant specimens. Other types of plant containers and growing mediums are possible.

The detector may comprise a detector sensitive for at least one type of rays. Preferably, the detector may comprise a detector for electromagnetic waves and more preferably a detector for light in at least one spectral wave length region selected from a visible, an infrared and ultraviolet wavelength region and most preferably a camera. The camera may be a digital camera, preferably with spatial and/or time resolution. The term detector further may comprise a detection system, comprising at least one optical element being chosen from: a mirror, a lens, a telescope, a microscope, an iris, a filter, an electro optical component, a magneto optical component and a birefringent element. Other types of detectors may be possible.

The selection device may be adapted to successively select different single plant specimens or groups of plant specimens from the plurality of plant specimens for imaging by the detector. The selection device may also be adapted to successively select all plant specimens from the plurality of plant specimens. A group of plant specimens e.g. may comprise at least one single plant specimen or a row of plant specimens. A single plant specimen may comprise a complete plant or parts of plants, like leafs, flowers, roots or stamps. A group of plant specimens may comprise complete plants and/or parts of plants which are not covered by the growing medium and/or parts of plants which are covered by the growing medium.

The detector may comprise at least one image-sensitive detector element, preferably at least one sensor chip having an at least two-dimensional array of radiation-sensitive elements and more preferably a CCD-chip and/or a CMOS-chip.

The deflection device may comprise at least one optical element selected from the group consisting of a mirror and a prism. The deflection device may be a device being able to deflect electromagnetic waves, e.g. light. The term "deflect" may comprise that the direction of the electromagnetic waves, e.g. the direction of propagation of the electromagnetic waves, may be changed. Thus, any material suitable for changing the direction of the electromagnetic waves may be suitable, e.g. as deflection device. The deflection device may be a device being able to change the direction of propagation of at least a part of electromagnetic waves, e.g. by reflection and/or refraction and/or diffraction and/or deflection. The term mirror may comprise at least one optical mirror, at least one coated mirror and/or at least one uncoated mirror for reflecting infrared and/or near-infrared radiation and/or preferably for reflecting light in a visible range. The optical element may preferably be spatially controllable, e.g. by a device for changing an angle and/or a position of the optical element and/or the deflection device, e.g. by an automatically adjustable mirror and/or an automatically adjustable prism, preferably by using an automated motor. The deflection device may further comprise at least one additional optical element, like a lens, a telescope, a microscope, a filter, an iris, a glass plate, a birefringent element, an acousto optical element, a magneto optical element or an additional light source like a lamp or a laser.

The screening device may be adapted to create at least one side view image by using the deflection device. The term side view image, as used in the present invention may imply any type of image, as described above. Preferably, a side view image may be a similar image as an image if you would take a picture, preferably directly, e.g. without using the deflection device, from the side, preferably perpendicular on the plant specimen, preferably perpendicular on the plant seedling. The term perpendicular may comprise an angle between 65° and 115°, preferably between 75° and 105° and most preferably an angle between 80° and 100°. The side view image may be preferably an image showing the complete length of the plant specimen, especially of the seedling, which means the image may show the complete seedling with roots or without roots. The side view image should preferably be not too much distorted. The opposite of a side view image would be a top view image or a bottom view image, which may be taken additionally.

The detector may comprise at least one top view camera. A top view camera may be characterized by an image plane of the camera which may be parallel to the growing medium in the plant containers. The term parallel may comprise an angle smaller than 50°, smaller than 20° and most preferably under an angle smaller than 5°.

The screening device may be adapted to simultaneously acquire at least two images of the single plant specimen or of the group of plant specimens from at least two different perspectives.

The term simultaneously, as used in the present invention, may imply a time delay smaller 5 seconds, particularly a time delay smaller 2 seconds, specifically a time delay smaller 1 second or even a time delay smaller 500 ms, or 200 ms, or 100 ms. As used in the present invention, the expression from at least two different perspectives may refer to images from different imaging directions. For simultaneously acquiring at least two images of the single plant specimen or of the group of plant specimens from at least two different perspectives, the detector may be used. Preferably, one and the same detector may be used for acquiring the at least two images, e.g. one camera, imaging on the same CCD-chip or CMOS-chip.

The embodiment of the screening device, in cooperation with the detector, preferably the top-view detector, being adapted to simultaneously acquire at least two images of the single plant specimen or of the group of plant specimens from at least two different perspectives, is specifically advantageous in the field of high-throughput screening. Thus, as outlined above, one and the same detector may be used for acquiring images from at least two different perspectives, such as from a top view perspective and from a side view perspective, simultaneously. Specifically when using two-dimensional arrays or two-dimensional arrangements of plant specimens, a top-view detector may be used for simultaneously acquiring a top view image and a side view image of a plant specimen or group of plant specimens selected by the selection device. Therein, the top view detector specifically may reduce the risk of a collision or unwanted contact of the detector and one or more of the plant specimens and/or may increase the freedom of design regarding an optional motion system of the screening device, specifically for the purpose of two-dimensional positioning of the plant specimens.

The deflection device may be adapted to create or to be used for creating at least one first image of the single plant specimen or of the group of plant specimens from at least one first perspective with the detector. The screening device may be adapted to simultaneously further create at least one second image from at least one second perspective with the detector. In particular, the image may be divided in at least two regions. One region may comprise the first image and the other region may comprise the second image. The deflection device further may be adapted to create more than two different images simultaneously from different perspectives, e.g. by using more than one mirror and/or more than one prism or by changing an angle of the mirror and/or of the prism, e.g. quickly, preferably within less than 10 s, most preferably within less than 1 s to get several images from different perspectives combined with a top view image.

The images may comprise at least one first image created by using the deflection device and at least one second image comprising a direct view of the single plant specimen or the group of plant specimens. Particularly, the first image may be a side view image. The term direct view, as used in the present invention, may imply a view without redirection by a deflection device, e.g. a top view.

The screening device may be adapted to create at least one side view image by using the deflection device and further at least one of a top view image and a bottom view image. The bottom view image may be generated by a bottom view by using a transparent plant container, e.g. a transparent tray, and/or a transparent growing medium, such that roots may be imaged. In this way, most preferably three-dimensional imaging may be possible. The transparent plant container may comprise an optical filter element to prevent the transmission of light with wavelength which may support the growth of algae.

The screening device may comprise at least one shielding element. The shielding element may be adapted to create a background for at least one of the images. Furthermore, the shielding element may be adapted to prevent background radiation from entering and/or to select the single plant specimen or the group of plant specimens. The shielding element may comprise at least one optical screen, preferably a black background for blocking at least a part of the background light. The shielding element may partially block the electromagnetic waves propagating between the plant specimens and the detector or may at least partially block electromagnetic waves propagating between the selected single plant specimen and/or the selected group of plant specimens from the plurality of plant specimens.

The screening device may either be adapted to effect a relative movement of the selection device and the selected single plant specimen or the selected group of plant specimens. As used herein, the term relative movement may refer to a movement of the selection device or parts thereof, wherein the selected single plant specimen or the selected group of plant specimens stands still, or vice versa. Alternatively, both elements, i.e. the selection device or parts thereof and the selected single plant specimen or the selected group of plant specimens both may perform a movement. Similarly, the term transport direction may refer to a direction of the relative movement as defined above. Preferably, the selected single plant specimen or the selected group of plant specimens is moved through a gap between the deflection device and the shielding element.

The selection device further may comprise at least one motion system. The motion system may be adapted to adjust a relative positioning of the detector, the deflection device and the plurality of plant specimens for selecting the single plant specimen or the group of plant specimens. As used in the present invention, the expression adjusting a relative positioning may refer to a continuous or discontinuous, e.g. stepwise, relative positioning. The plant container may be stationary and the detector and/or the deflection device may move, or the plant container may move and the detector and the deflection device may be stationary, or all may move. The images may be taken while moving or while being stationary.

The motion system may comprise a motion stage. The motion stage may be adapted to continuously or discontinuously, e.g. stepwise, move at least parts of the screening device.

The motion system may further be adapted to subsequently transport the plurality of plant specimens and/or a plurality of plant containers to and from at least one screening station, wherein the screening station may comprise the detector. The screening station may comprise a screening position, which may or may not be part of the motion system or which may be connected to the motion system, in order to allow for a successive motion of the detector, and/or the deflection device and/or the plurality of plant specimens and/or the plant specimen and/or the group of plant specimens. More than one screening station may be provided. As used herein, the term "screening position" denotes a position and/or apparatus of the system, in which or by which at least one image may be taken. However, other types of functionality may be comprised in the screening station, such as control means and/or recording means and/or computer means or other types of functionality or combinations thereof.

The motion system may comprise at least one of: a transport belt; a conveyor system, preferably a belt conveyor and/or a roller conveyor. The motion system may comprise a closed loop system. The closed loop system may be adapted for repeatedly transporting all containers into the screening station. As used herein, the expression closed loop system may refer to a motion system being capable of transporting a plurality of plant containers in a predetermined order and/or the transport system may be capable of repeatedly and successively transporting the plant containers into the screening station in the predetermined order. Thus, preferably, the motion system may comprise a motion circle of arbitrary shape. The motion circle may be capable of repeatedly transporting each plant container to the screening station by using a first section of the motion circle and transporting the plant container from the screening station by using a second section of the motion circle. The second section may be connected to the first section, preferably outside the screening station. However, other motion systems may be possible, such as motion systems using one or more robots or other motion apparatuses for transporting the detector and/or the deflection device and/or the plurality of plant specimens and/or the plant containers into the screening station.

The motion system may be adapted to generate a relative motion of the detector and the plurality of plant specimens in a transport direction, wherein the screening device is adapted to acquire at least one image essentially perpendicular to the transport direction and/or perpendicular to a plane of the growing medium. Herein, the plane of the growing medium is a plane which is parallel to the surface of the growing medium. Herein, the expression essentially perpendicular to the transport direction refers to a situation in which an optical axis of the imaging and the transport direction define an angle of 60° to 120°, preferably 80° to 100° and more preferably 85° to 95° or even 90°. Similarly, the expression essentially perpendicular to the plane of the growing medium refers to a situation in which the optical axis of the imaging deviates from an orientation perpendicular to the plane of the growing medium by no more than 30°, preferably by no more than 20°, more preferably by no more than 10° or no more than 5°, and wherein, most preferably, the optical axis of the imaging is perpendicular to the plane of the growing medium.

In an alternative embodiment, the motion system may be adapted to generate a relative motion of the detector and the plurality of plant specimens, e.g. in a transport direction, wherein the screening device is adapted to acquire at least one image essentially parallel to the transport direction. The term parallel, as used in the present invention, generally may imply an angle between the imaging direction, the direction in which the image may be acquired, and the transport direction, between +/−30°, preferably between +/−10° and most preferably an angle of 0°.

The deflection device may comprise at least one reflective surface being essentially parallel to the transport direction and/or to the group of plant specimens to be imaged, such as to one or more rows of plant specimens. The term essentially parallel may, according to the present invention, be referred to an angle between the reflective surface and the transport direction and/or the group of plant specimens between +/−30°, preferably between +/−10° and most preferably an angle of 0°.

In an alternative embodiment, the deflection device may comprise at least one reflective surface being essentially perpendicular to the transport direction and/or to the group of plant specimens to be imaged, such as to one or more rows of plant specimens. The term essentially perpendicular may, according to the present invention, be referred to an angle between the reflective surface and the transport direction and/or the group of plant specimens between 120° and 60°, preferably between 100° and 80° and most preferably the angle may be 90°.

The screening device may comprise at least one reader. The reader may be adapted to read at least one information from at least one identifier. The motion system may be designed to adjust a relative position between the reader and the identifier. The at least one identifier may preferably be at least one contactless identifier and more preferably at least one contactless electronic identifier, most preferably at least one RFID (Radio-frequency identification). The identifier may be assigned to a single plant specimen or a group of plant specimens. Preferably, the identifier may be or may comprise one or more of the following identifiers: a barcode; a contactless electronic identifier, i.e. an identifier comprising at least one piece of information, which may be read from the identifier, preferably without any physical contact between a reading mechanism, preferably a reader, and the identifier, most preferably the identifier may be at least one radio frequency identification tag (RFID tag). However, alternatively or additionally, other types of identifiers are possible. Each plant container and/or each row and/or each single plant specimen and/or each group of plant specimens may comprise one or more identifiers. The at least one identifier may for example be comprised in the plant containers, or in front of the plant containers, such as by integrating the identifier into a material of the plant containers and/or on a surface of the plant containers, preferably on an outer surface, and/or by integrating the identifier in an interior space of the plant containers, such as by implementing the identifiers into the growing medium inside the plant containers and/or by implementing the identifiers onto or into the plants contained in the plant containers. The information may be a simple identification, e.g. a number of plant specimens and/or of a row and/or growth conditions. Alternatively or additionally, other types of implementation of the identifiers into the plant containers and/or the group of plant specimens and/or the single plant specimen may be possible. In general, the at least one identifier not necessarily has to be in physical contact with the plant container and/or the plant specimen, but should be assigned to a respective plant container and/or the group of plant specimens and/or the single plant specimen in any unambiguous way.

The screening device may comprise at least one image analysis device. The image analysis device may be adapted to perform at least one image analysis of at least one of the images, preferably the image analysis device may be adapted to generate at least one growth parameter of the single plant specimen or the group of plant specimens. The image analysis device furthermore may be adapted to extract individual plant specimen data, e.g. seedling data, e.g. plant height and/or leaf width and/or leaf area and/or leaf color and/or root length and/or root width and/or root colors and/or root branching and/or other characteristics of the leafs and/or the roots and/or other plant specimens and/or resonance frequencies.

The image analysis device may be adapted to generate at least one growth parameter of the single plant specimen or the group of plant specimens. The term generate according to the present invention may refer to deriving e.g. from the image analysis. The image analysis device may use one or more physical principles, in order to measure the at least one growth parameter of the plant specimens. One or more growth parameters may be derived, which may comprise at least one condition, e.g. at least one growth condition, e.g. humidity and/or light intensity and/or temperature and/or air composition and/or growing medium composition. At least one measuring moment may be required to evaluate the evolution of a certain growth parameter. The growth parameter may be derived, such as one or more color parameters and/or a projected area and/or a volume of the plant specimen or the group of plant specimens and/or a root projected area and/or a root volume of the plant specimen or the group of plant specimens and/or a plant specimen's height and/or a biomass of the plant specimen or the group of plant specimens and/or a combination of the named and/or other parameters. The volume of the plant specimen and/or the root volume e.g. may be derived or approximated by using at least the first image and the second image.

The screening device further may have at least one database for recording data regarding the plant specimens. The data preferably may be at least one of the following: at least one image of the single plant specimen or of the group of plant specimens; at least one growth parameter derived from at least one image of the single plant specimen or of the group of plant specimens; information from the identifier. The database may comprise one type of suitable storage device, as a function of time and/or as a function of a plant specimen or a group of plant specimens. As outlined above, the at least one growth parameter may comprise one or more parameters characterizing the growth of the plant specimen or the group of plant specimens. The at least one growth parameter may preferably be chosen from: a height of the plant specimen; a width of the plant specimen; a color parameter or color parameters of the plant specimen; a number of leafs; at least one structure of the plant specimen; a presence of flowers in the plant specimen; a parameter characterizing the volume of the biomarkers of the plant specimen; a parameter characterizing the biochemical content of the plant specimen and/or the growing medium inside the plant container; a parameter characterizing the root growth in the plant specimen. However, other types of parameters and/or combinations of the named parameters and/or other parameters may be possible.

The screening device may be adapted to repeatedly acquire images of each single plant specimen or of each group of plant specimens, preferably with a time delay in between each acquiring. The time delay may be a time delay smaller than 1 month, preferably a time delay smaller than 1 week, more preferably smaller than 2 days, e.g. smaller than 1 day, or smaller than 1 hour, e.g. for a growth control time delays of 1 to 2 days may be useful, for testing herbicides or other chemical agents time delays of 1 to 3 hours may be useful.

The screening device furthermore may comprise a control system which may be adapted to control and/or to drive the image analysis device and/or the reader and/or the selection device and/or the motion system and/or the detector and/or the database and/or a power supply. The control system may comprise a computer and electrical and/or signal connectors, preferably electrical lines and interfaces.

The detector may be the top view camera, wherein the top view camera and the deflection device, preferably only one deflection device, e.g. a single mirror, may be adapted for selecting the single plant specimen or the group of plant specimens from the plurality of plant specimens. The selection device may comprise the deflection device, e.g. the single mirror. The deflection device may be adapted for being used to take at least the side view image by imaging the plant specimens. Most preferably, the screening device may be adapted for being used to take the side view image and the top view image, e.g. simultaneously, preferably by using one and the same detector and/or one and the same deflection device, e.g. one and the same mirror. Thus, preferably only the top view camera and the deflection device may be used for making a selection. At least the side view image may be taken when imaging the plant specimens, e.g. the plants, by use of this one deflection device.

The top view image may be generated by collecting electromagnetic waves, e.g. light, being emitted and/or reflected from the single plant specimen or the group of plant specimens directly, by using the detector. Preferably, the top view of the plant specimen and/or at least one side of the plant specimen may be imaged directly. The side view image may be generated by collecting electromagnetic waves, e.g. light, being emitted and/or reflected from a side of the single plant specimen or the group of plant specimens by using the deflection device, e.g. the single mirror, and the detector. The two images, preferably the top view image and the side view image, may be captured by one single shot of the detector, e.g. by one single shot of the camera. The two images preferably may appear on the detector and/or on the sensor chip, e.g. next to each other. The output of the screening device may comprise the top view image and/or the side view image. The output of the screening device may comprise the electromagnetic waves generating the images, e.g. the top view image and/or the side view image. The screening device may be adapted for acquiring more than one spatially resolved image, e.g. from different perspectives, e.g. the side view image and the top view image, by only one shot of the detector, preferably simultaneously. The shot of the detector may be an event of the detector and/or a step in a method of acquiring the images by the detector. The shot may comprise exposing the detector and/or the sensor chip, e.g. the CCD-chip and/or the CMOS chip, to the electromagnetic waves, preferably to the light. The shot may comprise a triggering of a shutter release. The shot may comprise opening at least one shutter. The shutter may be comprised by the detector. The shutter may also be separated from the detector. The shutter may be a device which may be adapted to switch between two states of the detector, wherein the detector may not be able to take an image in one state, e.g. a state wherein the shutter is closed and/or off, wherein in the other state the detector may be able to take at least one image, e.g. comprising the side view image and the top view image, or e.g. taking two images one after the other, e.g. first the side view image and then the top view image, wherein in this state the shutter may be opened and/or on. The shutter may comprise at least one electronic shutter and/or at least one mechanical shutter. The electronic shutter may be a device, which may turn on and/or off the sensor chip. The mechanical shutter may be a device, which may remove a device blocking the electromagnetic waves before reaching the detector and/or the sensor chip. The shot may comprise at least one read-out and/or at least one storage process and/or at least one information transfer process. The shot may be started by at least one triggering signal, e.g. a triggering signal provided by the computer. The shot may start by opening the shutter and the shot may be finished by closing the shutter. The image, most preferably comprising the side view image and/or the top view image, may be taken by using the detector during one shot of the detector. The top view image may be taken directly and the side view image may be taken by using the deflection device, e.g. the mirror. The deflection device and/or the detector may be adapted to be moved between the plurality of plant specimens and/or the single plant specimen and/or the group of plant specimens and/or between and/or over the plant container, e.g. by using at least a part of the motion system. In general, the screening device may comprise more than one deflection device and/or more than one detector and/or more than one selection device.

In a further aspect of the present invention, a method for screening at least one plant specimen in a plurality of plant specimens is disclosed. In the methods for screening at least one plant specimen in a plurality of plant specimens, preferably the screening device described above is used, wherein at least one detector is used. The detector acquires spatially resolved images. Further, at least one selection device is used. The selection device selects a single plant specimen or a group of plant specimens from the plurality of plant specimens for imaging by the detector. The selection device comprises at least one deflection device. The deflection device deflects electromagnetic waves propagating between the plant specimens and the detector. The deflection device is used for said imaging by the detector. The detector may acquire at least one image by use of the deflection device.

With regard to potential embodiments of the method according to the present invention, reference may be made to the above-mentioned screening device for screening at least one plant specimen in a plurality of plant specimens. Thus, the method for screening at least one plant specimen according to the present invention may be performed by using a screening device according to the present invention. Thus, reference may be made to the embodiments and definitions disclosed above. However, other types of systems may be used.

In a further aspect of the present invention, a tracking method for tracking growth conditions of a plurality of plant specimens is disclosed. A plurality of plant specimens are growing in growing medium in at least one plant container, alternatively, a plurality of plant containers comprise at least one plant specimen growing in growing medium. The method for screening at least one plant specimen in a plurality of plant specimens as described above is used for screening the plant specimens. At least one growth parameter is derived from the images. Preferably, for each single plant specimen or each group of plant specimens one growth parameter is derived from the images. The growth parameter is stored in a database. The growth parameter preferably is stored in a database as a function of time and/or as a function of the single plant specimen or as a function of the group of plant specimens and/or as a function of the row and/or as a function of the plant container.

Thus, as used herein, the term tracking method for tracking growth conditions may be referred to a method, which, in addition to simply monitoring the growth conditions, may make use of at least one database, in order to generate a tracking record of e.g. a growth parameter in each plant container, such as for later comparison of the growing results with the tracking record of the growing conditions. The term monitoring, as used herein, refers to observing one or more relevant parameters, such as by measuring or observing these parameters on a regular or irregular basis and/or at predetermined points in time. The term recording, as used herein, refers to the activity of monitoring one or more parameters and to store the results of the monitoring in a data storage.

Further, in addition to the at least one growth parameter measurement, e.g. derived from an image for each single plant specimen or each group of plant specimens, the database may contain further information. Thus, as outlined above, the growth parameter in each plant container and/or in each group of plant specimens may be stored as a function of time and/or as a function of plant specimen and/or plant container and/or a row and/or a group of plant specimens. Additionally or alternatively, the at least one database may comprise further data. At least one growth parameter is derived from the images, preferably for each single plant specimen or group of plant specimens, wherein the growth parameter is stored in a database, preferably as a function of time and/or as a function of the single plant specimen or group of plant specimens and/or as a function of the row and/or as a function of the plant container. With regard to potential growth parameters, reference may be made to the disclosure of potential growth parameters as listed above.

Besides simply recording data, the tracking method may further comprise one or more steps of evaluating the data or part of the data comprised in the at least one database. Thus, the tracking method may further comprise at least one method step in which, by comparing the growth parameters of the single plant specimen or of the group of plant specimens, e.g. an optimum of a certain growth parameter may be derived.

Further, additionally or alternatively to one or more evaluation steps, the tracking method may comprise one or more testing steps, in which the reaction of the plant specimens to specific growing conditions, e.g. stress conditions, may be tested, e.g. for analyzing stress resistance.

As used herein, the term stress resistance of growing plant specimens refers to a degree of capability of specific plant specimens of continuing their growing process in a more or less unaffected way despite of deviating, e.g. detrimental, growing conditions, such as reduced or lack of water, salty water, salty growing medium, reduced or lack of nutrients, non-optimum ambient temperatures, an effect of fungi and/or use of fungicides and/or effect of insects and/or use of insecticides and/or temperature treatments and/or chemicals and/or light and/or nutritional levels or combinations thereof. Thus, the term stress refers to non-optimum growing conditions, such as one or more of the non-optimum growing conditions mentioned before.

For example, a drought test and/or drought condition test and/or a water use efficiency test may be performed in which a variety of plant specimens may be subjected to a lack or reduced amount of water over a period of time, wherein the plant specimens' reaction to the lack of water may be recorded and/or monitored. The drought test and/or drought condition test may comprise one or more steps. Further, the tracking method may comprise at least one step wherein a drought resistance and/or water use efficiency of the plant specimens is monitored and/or recorded. Thus, again, one or more growth parameters and/or the time development of this at least one growth parameter may be recorded and/or evaluated, in order to qualify and/or quantify the plant specimens reaction to the lack of water or reduced amount of water. In the same way, a nutrient, e.g. nitrogen, use efficiency test may be performed in which a variety of plant specimens may be subjected to a lack or reduced amount of nutrients over a period of time, wherein the plant specimens' reaction to the lack of nutrient may be recorded. Further in the same way, salt stress or cold or heat stress may be tested.

As an example, a greenness index may be used and may be recorded over a period of time, during which the drought test and/or water use efficiency test or alternatively a nitrogen use efficiency test or other test may be performed, and the greenness index and/or the time development of the greenness index may be used to qualify and/or quantify the plant specimens reaction to the drought test and/or water use efficiency test. Within this drought test and/or water use efficiency test, the plurality of plant specimens may comprise a plurality of plant specimens, which are subjected to the same drought test and/or water use efficiency test, or, alternatively or additionally, a plurality of plants specimens of the same type may be subjected to different types of drought tests and/or water use efficiency tests, such as by subjecting the variety of plant specimens of the same type to a lack or reduced amount of water to a different degree, in order to evaluate the sensitivity of the plant specimens reaction to the lack or reduced amount of water. Other types of drought tests and/or water use efficiency tests are possible and known to the skilled person.

A drought resistance and/or water use efficiency of the plant specimens may be evaluated and/or monitored. Thus, such as by evaluating specific growth parameters, e.g. the greenness index, the resistance of the plant specimens to a lack of water or reduced amount of water may be compared and/or evaluated qualitatively and/or quantitatively. By comparing the added amount of liquid with the plants drought resistance, the water use efficiency of the plant specimens may be monitored.

The screening device according to the present invention, described above, may be used in a method for breeding plant specimens. The method may comprise the steps of growing a plurality of plant specimens of at least one species in at least one plant container. The plant specimens may be successively transported to and from the screening station by the motion system. The screening station may comprise the detector. Optionally, at least two images of the plant specimens from at least two different perspectives may be acquired simultaneously by using the detector. At least one growth parameter of the plant specimens in the screening station may be derived from the images. As used herein, the term breeding refers to any type of reproduction of plants, including the selection of plants or plant specimens with specific desired characteristics for propagation. Further, the term plant breeding may comprise more complex techniques, such as the selection of at least one specific phenotypic and/or genotypic characteristic, such as by evaluating specific plant parameters and/or growth parameters and/or genetic characteristics. In addition to the selection of specific plants or plant specimens, the breeding may comprise one or more other steps, such as the steps of generating seedlings of selected single plant specimen or the selected group of plant specimens.

The term "breeding" as used herein, refers to the study of the effect of genetic variation and/or varying conditions on phenotype and preferably is not directed to the actual step of sexual crossing and selecting.

The method for breeding plants according to the present invention may comprise at least one plant container, preferably a tray, which may be charged with growing medium of uniform characteristics. As used herein, the term uniform characteristics refers to growing media in different plant containers, which are identical as far as possible with common techniques, such as growing media which are taken from the same supply of a growing medium. Thus, at least macroscopically and, more preferably, chemically, the growing conditions provided by the growing media in different plant containers may be identical at least to the point of experimental uncertainty. Within the method for breeding plants, the plant containers may be successively transported to and from a screening station by at least one motion system, such as by using the system as disclosed above.

Within the method for breeding plant specimens, the plant containers may be successively transported to and from a screening station by at least one motion system, such as by using the screening device as disclosed above.

Further, the method for breeding plants according to the present invention may comprise a growing of the plurality of plant specimens in an environment of controlled climatic conditions, with controlled supply of liquid and changing the positions of the plant specimens within the environment as required to ensure at least substantially uniform exposure of all plant specimens to conditions in the environment. The method further may comprise the step of selecting plant specimens for further breeding or for commercial use by comparing phenotypic characteristics of the plant specimens.

The term environment of controlled climatic conditions, as used herein, may refer to an environment of the plant containers in which at least one climatic parameter may be adjusted to one or more specific, predetermined values. Thus, the environment of controlled climatic conditions may comprise an environment, in which the ambient temperature is adjusted to at least one predetermined temperature, which may be static or may be subjected to a time development. The control may comprise a control to a specific temperature value within an experimental uncertainty of less than 1° Kelvin or less, such as to 0.5° Kelvin. The controlled climatic conditions may comprise a regulation of the climatic conditions, such as by using at least one controller or regulator, in order to regulate the climatic conditions to at least one predetermined value.

Further, as used herein, the term controlled supply of liquid may refer to the fact that a supply of liquid to each plant container is performed in a predetermined way, such as by using the system according to the present invention in one or more of the embodiments disclosed above. Thus, the controlled supply of liquid may comprise a predetermined rate of liquid supply to each plant container. Thus, as outlined above, one or more watering stations may be used in order to control the supply of liquid.

Further, the method for breeding plant specimens according to the present invention may comprise a changing of the positions of the plant containers within the environment as acquired to ensure at least substantially uniform exposure of all plants in a plant container to conditions in the environment. In other words, in case there are N potential positions of the plant containers in the environment, the method is performed in such a way that the amount of time spent in position E, with E=1 to N, is substantially equal for all plant containers, which, preferably, means that the variation in between the containers is less than 1 h, preferably less than 10 min and more preferably less than 1 min. However, the amount of time each plant container is positioned in the potential positions may vary in between different positions.

Again, this changing of positions may be performed by using a system according to the present invention and as disclosed in one or more of the embodiments above. Preferably, at least one motion system is used. By using this method, variations of the growing conditions of the plants in the plant containers which are due to different locations in the environment may be reduced to a minimum. The method for breeding plant specimens according to the present invention further may comprise the step of selecting plant specimens for further breeding or for commercial use by comparing the phenotypic characteristics of the plant specimens. As used herein, the term phenotypic characteristics refers to at least one observable characteristic or trait of the plant specimen, such as at least one morphological parameter or a time development of the at least one morphological parameter. Thus, the at least one phenotypic characteristic which may be used for comparison of the plants may comprise one or more of the growth parameters and/or one or more of the morphological parameters and/or the time development of these parameters, such as one or more of the growth parameters and/or one or more of the morphological parameters and/or one or more resistances, such as the resistance to at least one drought test, or reduced nutrient availability.

In a further aspect of the present invention, use of the screening device in a method for improved growing of plant specimens for phenotyping, for selecting the most desired phenotypes based on genotype scoring, is disclosed. As used herein, the term phenotyping refers to the monitoring of one or more phenotypic characteristics of plant specimens. Further, as used herein, the term genotype refers to a genetic constitution of the plant specimens. The term phenotypic scoring refers to a qualitative or quantitative comparison of the results of the phenotyping as disclosed above, such as to a qualitative and/or quantitative comparison of one or more phenotypic characteristics. This scoring may be performed on a quantitative scale, such as by using at least two classes for classifying the phenotypic characteristics of the plant specimens.

The method for improved growing of plant specimens for phenotyping uses the screening device according to the present invention, as described above, wherein the method comprises successively transporting the plant specimens to and from the screening station by the motion system, wherein the screening station comprises the detector. The detector may make one image using the deflection device. Optionally, at least two images of the plant specimens from at least two different perspectives may be acquired simultaneously by using the detector. At least one growth parameter of the plant specimens in a screening station may be derived from the images. The method further comprises the step of controlling at least one growth condition of the plant specimens.

The method for improved growing of plant specimens for phenotyping may further comprise displacing the plant specimens automatically during their growing cycle so as to avoid extended exposure to a particular microenvironment. Thus, reference may be made to the method for breeding plant specimens as disclosed above and to the at least one step of changing the positions of the plant containers of this method. Specifically, a screening device according to the present invention may be used, which comprises one or more motion systems and/or one or more transport systems. Thus, reference may be made to the embodiments disclosed above.

In a further aspect of the present invention, a method for rapid analysis of stress resistance of growing plant specimens is disclosed.

As used herein and as discussed above, the term stress resistance of growing plant specimens may refer to a degree of capability of specific plant specimens of continuing their growing process in a more or less unaffected way despite of deviating, e.g. detrimental, growing conditions, such as reduced or lack of water, salty water, salty growing medium, reduced or lack of nutrients, non-optimum ambient temperatures, an effect of fungi and/or use of fungicides and/or effect of insects and/or use of insecticides and/or temperature treatments and/or chemicals and/or light and/or nutritional levels or combinations thereof. Thus, the term stress refers to non-optimum growing conditions, such as one or more of the non-optimum growing conditions mentioned before.

The term rapid analysis refers to a quantitative and/or qualitative evaluation of the stress resistance of at least one growing plant specimen, preferably the comparison of stress resistances of different types of growing plant specimens, on a short time scale, such as on a time scale comprising no more than 5 growing cycles, preferably no more than 2 or most preferably no more than 1 growing cycle or even less, such as a time scale of 5 months or less, preferably 3 months or less or even 1 month or less. The term "growing cycle" refers to a biological process in plant specimens recurring within characteristic time scales, preferably periodically, e.g. starting from germination, plant growth, fertilization and ending with seed production. A growing cycle may comprise at least one further growing cycle. The growing cycle and/or the characteristic time scale may be influenced by light intensity and/or temperature. A growing cycle may be e.g. characterized by a circadian rhythm. The method for rapid analysis of stress resistance of growing plant specimens uses the screening device according to the present invention and comprises: growing the plant specimens under stress conditions; successively transporting the plant specimens to and from a screening station by a motion system, wherein the screening station comprises the detector. The detector may make one image using the deflection device. Optionally, at least two images of the plant specimens from at least two different perspectives may be acquired simultaneously by using the detector. The method further comprises the step of deriving at least one growth parameter of the plant specimens in the screening station from the images; and analyzing the stress resistance of the plant specimens based on the growth parameter.

As outlined above, the stress conditions may comprise any type of non-optimum growing conditions or combinations thereof.

The screening device, the use of the screening device and methods according to the present invention may e.g. be very useful for testing transgenic plants for the effect of a specific gene or gene combination which is over- or underexpressed or even knocked down. On the other hand, the screening device and methods may be used to evaluate stress resistance, such as a resistance against a drought stress and/or salt stress and/or any other type of stress or deviating growing condition, e.g. as described above.

Further, additionally or alternatively, water use efficiency or any other characteristics of the plants may be evaluated. Stress resistance measurements may be based on humidity measurements, such as by using the well-known fact that a plant specimen, which uses less water and, thus, evaporates less water, typically is in a worse physical condition than a plant specimen using more water.

Summarizing the ideas of the present invention, the following embodiments are preferred:

Embodiment 1

A screening device for screening at least one plant specimen in a plurality of plant specimens, the screening device comprising a detector adapted for acquiring spatially resolved images, the screening device further comprising a selection device adapted for selecting a single plant specimen or a group of plant specimens from the plurality of plant specimens for imaging by the detector, the selection device comprising at least one deflection device adapted for deflecting electromagnetic waves propagating between the plant specimens and the detector.

Embodiment 2

The screening device according to one of the preceding embodiments, the screening device further comprising at least one plant container containing a plurality of plant specimens or a plurality of plant containers containing at least one plant specimen, preferably the plant specimens growing in rows.

Embodiment 3

The screening device according to one of the preceding embodiments, wherein the detector comprises a detector sensitive for at least one type of rays, preferably a detector for electromagnetic waves and more preferably a detector for light in at least one spectral wavelength region selected from a visible, an infrared and ultraviolet wavelength region and most preferably a camera.

Embodiment 4

The screening device according to one of the preceding embodiments, wherein the selection device is adapted to successively select different single plant specimens or groups of plant specimens from the plurality of plant specimens for imaging by the detector.

Embodiment 5

The screening device according to the preceding embodiment, wherein the selection device is adapted to successively select all plant specimens from the plurality of plant specimens.

Embodiment 6

The screening device according to one of the preceding embodiments, wherein the detector comprises at least one image-sensitive detector element, preferably at least one sensor chip having an at least 2-dimensional array of radiation-sensitive elements and more preferably a CCD-chip and/or CMOS-chip.

Embodiment 7

The screening device according to one of the preceding embodiments, wherein the deflection device comprises at least one optical element selected from the group consisting of a mirror and a prism.

Embodiment 8

The screening device according to the preceding claim, wherein the deflection device comprises at least one reflective surface being essentially parallel to a transport direction of the plant specimens and/or parallel to the group of plant specimens, preferably parallel to a row of plant specimens.

Embodiment 9

The screening device according to one of the preceding embodiments, wherein the screening device is adapted to be used for creating at least one side view image by using the deflection device.

Embodiment 10

The screening device according to one of the preceding embodiments, wherein the detector comprises at least one top view camera.

Embodiment 11

The screening device according to one of the preceding embodiments, wherein the screening device is adapted to simultaneously acquire at least two images of the single plant specimen or of the group of plant specimens from at least two different perspectives by using the detector.

Embodiment 12

The screening device according to the preceding embodiment, wherein one and the same detector is used for acquiring the at least two images, preferably by imaging the at least two images onto one and the same image-sensitive detector element, such as one and the same CCD-chip and/or CMOS-chip.

Embodiment 13

The screening device according to one of the two preceding embodiments, wherein the deflection device is adapted to be used for creating at least one first image of the single plant specimen or of the group of plant specimens from at least one first perspective with the detector, wherein the screening device is adapted to simultaneously further create at least one second image from at least one second perspective with the detector.

Embodiment 14

The screening device according to one of the two preceding embodiments, wherein the images comprise at least one first image created by using the deflection device and at least one second image comprising a direct view of the single plant specimen or the group of plant specimens.

Embodiment 15

The screening device according to one of the three preceding embodiments, wherein the screening device is adapted to create at least one side view image by using the deflection device and further at least one of a top view image and a bottom view image.

Embodiment 16

The screening device according to one of the preceding embodiments, the screening device comprising at least one shielding element, the shielding element being adapted to create a background for at least one of the images.

Embodiment 17

Screening device according to the preceding embodiment, wherein the screening device is adapted to effect a relative movement of the selection device and the selected single plant specimen or the selected group of plant specimens, preferably by using at least one motion system and/or by using at least one motion stage, wherein the selected single plant specimen or the selected group of plant specimens are moved through a gap between the deflection device and the shielding element.

Embodiment 18

The screening device according to one of the preceding embodiments, the selection device further comprising at least one motion system, the motion system being adapted to adjust a relative positioning of the detector, the deflection device and the plurality of plant specimens for selecting the single plant specimen or the group of plant specimens.

Embodiment 19

The screening device according to the preceding embodiment, wherein the motion system comprises a motion stage.

Embodiment 20

The screening device according to one of the two preceding embodiments, wherein the motion system is adapted to subsequently transport the plurality of plant specimens and/or a plurality of plant containers to and from at least one screening station, wherein the screening station comprises the detector.

Embodiment 21

The screening device according to one of the three preceding embodiments, wherein the motion system comprises at least one of: a transport belt; a conveyor system, preferably a belt conveyor and/or a roller conveyor.

Embodiment 22

The screening device according to one of the four preceding embodiments, wherein the motion system comprises a closed loop system.

Embodiment 23

The screening device according to one of the five preceding embodiments, wherein the motion system is adapted to generate a relative motion of the detector and the plurality of plant specimens in a transport direction, wherein the screening device is adapted to acquire at least one image essentially perpendicular to the transport direction.

Embodiment 24

The screening device according to the preceding embodiment, the deflection device comprising at least one reflective surface being essentially parallel to the transport direction and/or parallel to the group of plant specimens, preferably parallel to a row of plant specimens.

Embodiment 25

The screening device according to one of the preceding embodiments, wherein the screening device comprises at least one reader, wherein the reader is adapted to read at least one information from at least one identifier, preferably at least one contactless identifier and more preferably at least one contactless electronic identifier, most preferably at least one RFID, the identifier being assigned to the single plant specimen or to the group of plant specimens.

Embodiment 26

The screening device according to one of the preceding embodiments, the screening device comprising at least one image analysis device, the image analysis device being adapted to perform at least one image analysis of at least one of the images, preferably the image analysis device is adapted to generate at least one growth parameter of the single plant specimen or the group of plant specimens.

Embodiment 27

The screening device according to the preceding embodiment, wherein the image analysis device is adapted to generate at least one growth parameter of the single plant specimen or the group of plant specimens.

Embodiment 28

The screening device according to one of the preceding embodiments, the screening device further having at least one database for recording data regarding the plant specimens, preferably at least one of the following: at least one image of the single plant specimen or of the group of plant specimens; at least one growth parameter derived from at least one image of the single plant specimen or of the group of plant specimens; information from at least one identifier.

Embodiment 29

The screening device according to one of the preceding embodiments, the screening device being adapted to repeatedly acquire images of each single plant specimen or of each group of plant specimens, preferably with a time delay in between each acquiring.

Embodiment 30

A method for screening at least one plant specimen in a plurality of plant specimens, preferably by using the screening device according to the preceding embodiments, wherein at least one detector is used, wherein the detector acquires spatially resolved images, wherein further at least one selection device is used, wherein the selection device selects a single plant specimen or a group of plant specimens from the plurality of plant specimens for imaging by the detector, wherein the selection device comprises at least one deflection device, wherein the deflection device deflects electromagnetic waves propagating between the plant specimens and the detector, and wherein the deflection device is used for said imaging by the detector.

Embodiment 31

A tracking method for tracking growth conditions of a plurality of plant specimens, wherein a plurality of plant specimens are growing in growing medium in at least one plant container, alternatively, a plurality of plant containers comprise at least one plant specimen growing in growing medium, wherein the method according to the preceding method embodiment is used for screening the plant specimens, wherein at least one growth parameter is derived from the images, preferably for each single plant specimen or group of plant specimens, wherein the growth parameter is stored in a database, preferably as a function of time and/or as a function of the single plant specimen or group of plant specimens and/or as a function of the row and/or as a function of a plant container.

Embodiment 32

The tracking method according to the preceding embodiment, wherein a drought test and/or a water use efficiency test is performed in which a variety of plant specimens is subjected to a lack or reduced amount of water over a period of time, wherein the plant specimens' reaction to the lack of water is recorded and/or monitored.

Embodiment 33

The tracking method according to the preceding embodiment, wherein a drought resistance and/or water use efficiency of the plant specimens is monitored and/or recorded.

Embodiment 34

A method for breeding plant specimens, the method using the screening device according to one of the preceding embodiments referring to a screening device, the method comprising the steps of growing a plurality of plant specimens of at least one species in at least one plant container, wherein the plant specimens are successively transported to and from a screening station by a motion system, wherein the screening station comprises the detector, wherein the detector is used for taking at least one image of the plant specimens, preferably at least one image of each plant specimen, and more preferably at least two images of the plant specimens or at least two images of each plant specimen.

Embodiment 35

The method according to the preceding embodiment, wherein at least two images of the plant specimens from at least two different perspectives are acquired simultaneously by using the detector, wherein at least one growth parameter of the plant specimens in the screening station is derived from the images.

Embodiment 36

The method according to the preceding embodiment, wherein the at least one plant container is charged with growing medium of uniform characteristics.

Embodiment 37

The method according to one of the two preceding embodiments, wherein the plurality of plant specimens growing in an environment of controlled climatic conditions, with controlled supply of liquid and changing the positions of the plant specimens within the environment as required to ensure at least substantially uniform exposure of all plant specimens to conditions in the environment, and the method further comprising the step of selecting plant specimens for further breeding or for commercial use by comparing phenotypic characteristics of the plant specimens.

Embodiment 38

Use of the screening device according to one of the preceding embodiments referring to a screening device, in a method for improved growing of plant specimens for phenotyping, for selecting the most desired genotypes based on phenotype scoring, the method comprising:
  displacing the plant specimens automatically during their growing cycle so as to avoid extended exposure to a particular micro-environment;
  successively transporting the plant specimens to and from a screening station by a motion system, wherein the screening station comprises the detector, wherein at least one growth parameter of the plant specimens in the screening station is derived from the images; and
  controlling at least one growth condition of the plant specimens.

Embodiment 39

Use according to the preceding embodiment, the method further comprising displacing the plant specimens automatically during their growing cycle so as to avoid extended exposure to a particular micro environment.

Embodiment 40

Use according to one of the two preceding embodiments, wherein at least two images of the plant specimens from at least two different perspectives are acquired simultaneously by using the detector.

Embodiment 41

A method for rapid analysis of stress resistance of growing plant specimens, the method using the screening device according to one of the preceding embodiments referring to a screening device, the method comprising:
  growing the plant specimens under stress conditions;
  successively transporting the plant specimens to and from a screening station by a motion system, wherein the screening station comprises the detector, wherein at least one growth parameter of the plant specimens in the screening station is derived from the images; and
  analyzing the stress resistance of the plant specimens based on the growth parameter.

Embodiment 42

The method according to the preceding embodiment, wherein at least two images of the plant specimens from at least two different perspectives are acquired simultaneously by using the detector.

SHORT DESCRIPTION OF DRAWINGS

In the following, further potential details and features of the invention are disclosed in view of examples, preferably in connection with the dependent claims. The features disclosed in the examples and/or in the preferred embodiments may be realized in an isolated way or in any arbitrary combination. The invention is not restricted to the preferred embodiments and/or the examples. The examples are depicted in a figure in a schematic way. Identical reference numbers in the figures refer to identical, similar or functionally identical elements.

Figure 1B:
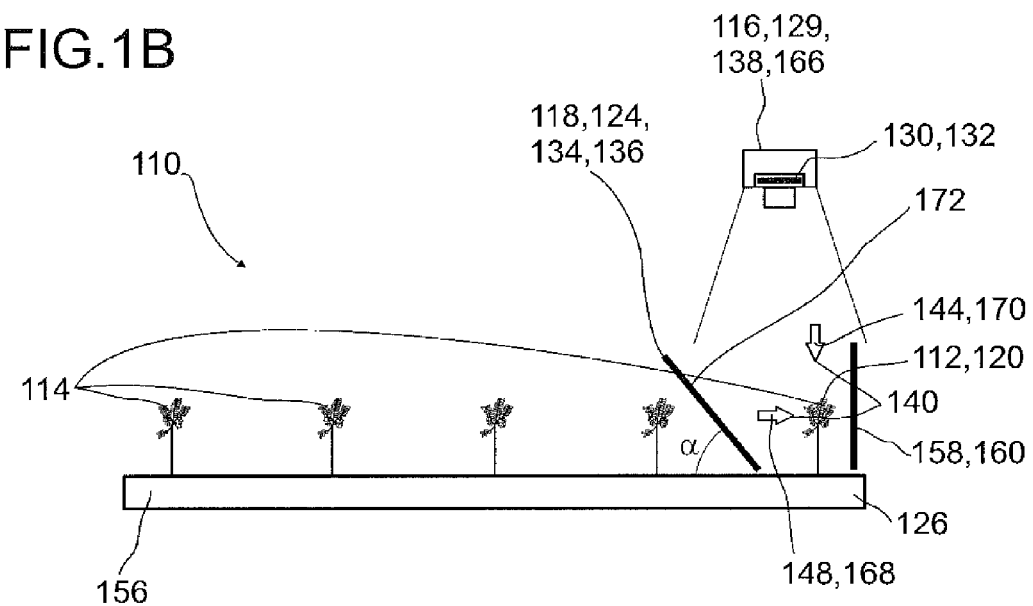
Figure 1C:
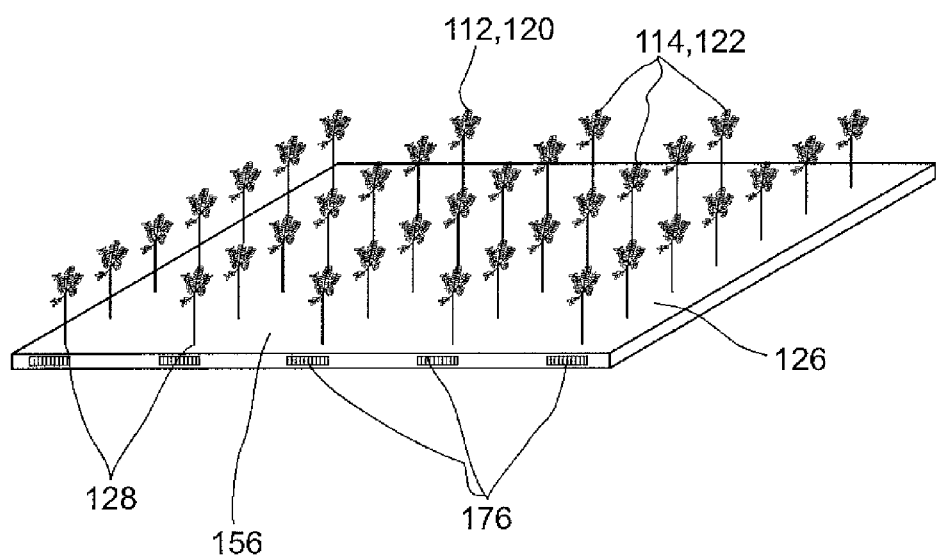

In the drawings:

FIG. 1A shows a perspective view of a screening device for screening at least one plant specimen in a plurality of plant specimens; and FIG. 1B shows a side view of a part of the screening device according to FIG. 1A; and FIG. 1C shows a perspective view of a plant container of the screening device according to FIG. 1A and FIG. 1B.

EXAMPLES

In FIGS. 1A and 1B an example of a screening device 110 for screening at least one plant specimen 112 in a plurality of plant specimens 114 is depicted. The screening device 110 comprises at least one detector 116 adapted for acquiring spatially resolved images 117. The screening device 110 further comprises at least one selection device 118 adapted for selecting a single plant specimen 120 or a group of plant specimens 122 from the plurality of plant specimens 114 for imaging by the detector 116. The selection device 118 comprises at least one deflection device 124 adapted for deflecting electromagnetic waves propagating between the plant specimens 112 and the detector 116.

The screening device 110 further may comprise at least one plant container 126 containing a plurality of plant specimens 114, preferably the plant specimens 112 growing in rows 128, or a plurality of plant containers 126 containing at least one plant specimen 112. FIG. 1A shows a screening device 110 for screening at least one plant specimen 112 in a plurality of plant specimens 114. FIG. 1C particularly shows a plant container 126, preferably a tray. Plant specimens 112, preferably plants having grass-like seedlings, like rice, may be germinated in plant containers 126, preferably trays, and sown in rows 128, preferably in lines, or rows arrays leaving sufficient space between these rows 128. The plant container 126 may be divided in small areas, e.g. in a lattice-like structure, preferably with one square for each plant specimen 112. In this example the small areas may be used to separate the plant specimens 112, e.g. to fluidly separate the plant specimens 112.

The detector 116 may be a detector 116 sensitive for at least one type of rays, preferably a detector 116 for electromagnetic waves and more preferably a detector 116 for light in at least one spectral wavelength region selected from: a visible region; an infrared and ultraviolet wavelength region. The detector 116 most preferably may be a camera 129. The detector 116, preferably the camera 129, may be a conventional optical camera 129 operating in a visible range, but may also be, but not limited to, an infrared, an near-infrared, a fluorescence, or another type of camera 129.

The selection device 118 may be adapted to successively select different single plant specimens 120 or groups of plant specimens 122 from the plurality of plant specimens 114 for imaging by the detector 116.

The selection device 118 may be adapted to successively select all plant specimens 112 from the plurality of plant specimens 114. In the example of the present invention described here, a single plant specimen 120 or a group of plant specimens 122, e.g. a row 128, from the plurality of plant specimens 114 may be selected for imaging by the detector 116.

The detector 116 may comprise at least one image-sensitive detector element 130, preferably at least one sensor chip 132 having an at least two-dimensional array of radiation-sensitive elements and more preferably a CCD-chip and/or a CMOS chip.

The detector 116 may comprise at least one top view camera 138.

The deflection device 124 may comprise at least one optical element 134 selected from the group consisting of a mirror 136 and a prism. The space between the rows 128, preferably between lines, may be sufficient to allow the deflection device 124 and/or the optical element 134, preferably an optical mirror 136, to be inserted between the rows 128.

The screening device 110 may be adapted to create at least one side view image 152 by using the deflection device 124.

The screening device 110 may be adapted to simultaneously acquire at least two images 117 of the single plant specimen 120 or of the group of plant specimens 122 from at least two different perspectives, indicated in FIG. 1B by two arrows 140, by using the detector 116. Each row 128 is imaged by inserting the deflection device 124, preferably the mirror 136, parallel to the row 128 of plant specimen 112, preferably seedlings, such that at least one image 117, preferably at least one side view image 152, in particular one reflected image 117, is within the camera view, as shown in FIGS. 1A and 1B. The deflection device 124 may be adapted to be used for creating at least one first image 146 of the single plant specimen 120 or of the group of plant specimens 122 from at least one first perspective 148 with the detector 116. Further, the screening device 110 may be adapted to simultaneously further create at least one second image 142 from at least one second perspective 144 with the detector 116.

The images 117 may comprise at least one first image 146 created by using the deflection device 124 and at least one second image 142 comprising a direct view 150 of the single plant specimen 120 or the group of plant specimens 122. The angle of the optical element 134, preferably of the mirror 136, may determine the area available for imaging. Preferably, two images 117 from two different perspectives, preferably two different views, may be obvious to the detector 116, preferably to the top view camera 138. The two views may comprise a side view and a top view resulting in a side view image 152 and/or a top view image 154. Thus, a side view image 152 and a top view image 154 may allow more plant specimens 112 to be imaged, preferably from a first perspective 148 and a second perspective 144.

The screening device 110 may be adapted to create at least one side view image 152 by using the deflection device 124 and further at least one of a top view image 154 and optionally a bottom view image. The plant container 126 may comprise at least one growing medium 156. If the growing medium 156 is transparent, roots may be imaged, preferably such as in vertical plates cultivation systems. If the plant container 126 is transparent, the roots can be imaged as described in WO2006/029987, which is hereby incorporated in its entirety.

The screening device 110 may comprise at least one shielding element 158. The shielding element 158 may be adapted to create a background 160 for at least one of the images 117.

The screening device 110 may either be adapted to transport the selected single plant specimen 120 or the selected group of plant specimens 122 to the deflection device 124 or may be adapted to transport the deflection device 124 between the selected single plant specimen 120 or a selected group of plant specimens 122.

In an alternative example, the screening device 110 may either be adapted to transport the selected single plant specimen 120 or the selected group of plant specimens 122 between the deflection device 124 and the shielding element 158 or may be adapted to transport the deflection device 124 and the shielding element 158 between the selected single plant specimen 120 or a selected group of plant specimens 122.

The selection device 118 may further comprise at least one motion system 162. The motion system 162 may be adapted to adjust a relative positioning of the detector 116, the deflection device 124, and preferably the shielding element 158, and the plurality of plant specimens 114 for selecting the single plant specimen 120 or the group of plant specimens 122.

Furthermore, the plant specimen 112, preferably seedlings, may be selected for imaging, e.g. for imaging by the detector 116, and/or for further breeding, e.g. for transplantation onto their destination containers, e.g. from high-density arrays. Therefore, the plant container 126, preferably the tray, may be inserted into an apparatus, preferably a motion system 162. The motion system 162 may move the plant container 126 or the plant containers 126 under the detector 116, preferably under a digital camera 129.

The motion system 162 may comprise a motion stage 164.

The motion system 162 may be adapted to subsequently transport the plurality of plant specimens 114 and/or a plurality of plant containers 126 or at least one plant container 126 to and from at least one screening station 166, wherein the screening station 166 may comprise the detector 116. An image 117, preferably a picture, may be taken and analyzed once the deflection device 124, preferably the mirror 136, may be in place, preferably at the screening station 166, and the identity of the plant specimen 112, 120 may be detected, e.g. by reading an identifier 176, as described below, or by analyzing the image. After one image 117 may be taken, the deflection device 124, preferably the at least one mirror 136, may be retracted and the plant container 126, preferably the tray, may be moved to another position, such that e.g. the next row 128 may be imaged.

The motion system 162 may comprise at least one of: a transport belt; a conveyor system, preferably a belt conveyor and/or a roller conveyor. Further, the motion system 162 may comprise a closed loop system, which is not shown in the figures. The motion system 162 may be adapted to generate a relative motion of the detector 116 and the plurality of plant specimens 114 in a transport direction 168. The screening device 110 may be adapted to acquire at least one image 117 essentially perpendicular to the transport direction 168. The term essentially perpendicular may comprise an angle between the imaging direction 170, the direction in which the image 117 may be acquired, and the transport direction 168. This angle may be between 120° and 60°, preferably between 100° and 80° and most preferably the angle may be 90°.

The deflection device 124 may comprise at least one reflective surface 172 being essentially parallel to the group of plant specimens 122, to be imaged. The term essentially parallel may refer to an angle between the reflective surface 172 and the group of plant specimens 122, preferably a row 128. This angle may be between +/−30°, preferably between +/−10° and most preferably this angle may be 0°.

The screening device 110 may comprise at least one reader 174, in the example shown in FIG. 1A preferably two readers 174, wherein the reader 174 may be adapted to read at least one information from at least one identifier 176. The identifier 176 may be at least one contactless identifier 176 and more preferably at least one contactless electronic identifier 176, most preferably at least one RFID. The identifier 176 may be assigned to the single plant specimen 120 or to the group of plant specimens 122, most preferably to the plant container 126, preferably a tray, and/or to each row 128, as shown in FIG. 1A and FIG. 1C. Each plant container 126, preferably each tray, each single plant specimen 120 and/or each group of plant specimens 122 and/or each row 128 may be identified by means of barcodes, RFID transponders or other contactless means of identification. The motion system 162 may be designed to adjust a relative position between the reader 174 and the identifier 176.

The screening device 110 may comprise at least one image analysis device 178. The image analysis device 178 may be adapted to perform at least one image analysis of at least one of the images 117, preferably the image analysis device may be adapted to generate at least one growth parameter of the single plant specimen 120 or the group of plant specimens 122. In the example of the present invention as shown in FIG. 1A, the image analysis device 178 preferably may be an automatic image analysis device 178 to perform an automatic image analysis to extract a single plant specimen 120 and/or a group of plant specimens 122, preferably an individual seedling data, like a plant height, and/or a leaf width, and/or a leaf area, and/or a leaf color and/or a root branching and/or resonance frequencies and/or any other information. Preferably, the image analysis device 178 may allow to calculate a proper selection data.

The image analysis device 178 may further be adapted to generate at least one growth parameter of the single plant specimen 120 and/or of the group of plant specimens 122, preferably of the seedling(s). The image analysis device 178 may be implemented in a computer 180, which may be provided with an image analysis software. One may be able to facilitate the extraction of target pixels, preferably by using the image analysis software.

The screening device 110 further may have at least one database 182 for recording data regarding the plant specimen 112. The data may preferably be at least one of the following: at least one image 117 of the single plant specimen 120 or of the group of plant specimens 122; at least one growth parameter derived from at least one image 117 of the single plant specimen 120 or of the group of plant specimens 122; information from at least one identifier 176.

The screening device 110 may be adapted to repeatedly acquire images 117 of each single plant specimen 120 or of each group of plant specimens 122, preferably with a time delay in between each acquiring. Thus, if the plant specimens 112, preferably the plantlets, are imaged more than once in time, a plant growth rate and/or a time course or other plant phenotypic traits such as individual seedling data and/or plant height and/or leaf width and/or leaf area and/or leaf color and/or root branching may be automatically calculated from two or more consecutive images 117.

Further, the screening device 110 may comprise additional detectors 116, like a finger camera 184, e.g. for taking side view images 152 or overview images of the screening device 110, preferably for controlling the screening. The screening device 110 may be surrounded by a housing 186.

The detector 116 may be the top view camera 138, wherein the top view camera 138 and the deflection device 124, preferably only one deflection device 124, e.g. a single mirror 136, may be adapted for selecting the single plant specimen 120 or the group of plant specimens 122 from the plurality of plant specimens 114. The selection device 118 may comprise the deflection device 124, e.g. the single mirror 136. The deflection device 124 may be adapted for being used to take at least the side view image 152 by imaging the plant specimens 112. Most preferably, the screening device 110 may be adapted for being used to take the side view image 152 and the top view image 154, e.g. simultaneously, preferably by using one and the same detector 116 and/or one and the same deflection device 124, e.g. one and the same mirror 136. Thus, preferably only the top view camera 138 and the deflection device 124 may be used for making a selection. At least the side view image 152 may be taken when imaging the plant specimens 112, e.g. the plants, by use of this one deflection device 124.

The top view image 154 may be generated by collecting electromagnetic waves, e.g. light, being emitted and/or reflected from the single plant specimen 120 or the group of plant specimens 122 directly, by using the detector 110, and preferably by not using the deflection device 124. Preferably, the top view of the plant specimen 120 and/or at least one side of the plant specimen 120 may be imaged directly. The side view image 152 may be generated by collecting electromagnetic waves, e.g. light, being emitted and/or reflected from a side of the single plant specimen 120 or the group of plant specimens 122 by using the deflection device 124, e.g. the single mirror 136, and the detector 110. The two images 117, preferably the top view image 154 and the side view image 152, may be captured by one single shot of the detector 116, e.g. by one single shot of the camera 129. The two images 117 preferably may appear on the detector 116 and/or on the sensor chip 132, e.g. next to each other. The output of the screening device 110 may comprise the top view image 154 and/or the side view image 152. The output of the screening device 110 may comprise the electromagnetic waves generating the images 117, e.g. the top view image 154 and/or the side view image 152. The screening device 110 may be adapted for acquiring more than one spatially resolved image 117, e.g. from different perspectives, e.g. the side view image 152 and the top view image 154, by only one shot of the detector 116, preferably simultaneously. The shot of the detector 116 may be an event of the detector 116 and/or a step in a method of acquiring the images 117 by the detector 116. The shot may comprise exposing the detector 116 and/or the sensor chip 132, e.g. the CCD-chip and/or the CMOS chip, to the electromagnetic waves, preferably to the light. The shot may comprise a triggering of a shutter release. The shot may comprise opening at least one shutter. The shutter may be comprised by the detector 116. The shutter may also be separated from the detector 116. The shutter may be a device which may be adapted to switch between two states of the detector 116, wherein the detector 116 may not be able to take an image in one state, e.g. a state wherein the shutter is closed and/or off, wherein in the other state the detector 116 may be able to take at least one image 117, e.g. comprising the side view image 152 and the top view image 154, or e.g. taking two images 117 one after the other, e.g. first the side view image 152 and then the top view image 154, wherein in this state the shutter may be opened and/or on. The shutter may comprise at least one electronic shutter and/or at least one mechanical shutter. The electronic shutter may be a device, which may turn on and/or off the sensor chip 132. The mechanical shutter may be a device, which may remove a device blocking the electromagnetic waves before reaching the detector 116 and/or the sensor chip 132. The shot may comprise at least one read-out and/or at least one storage process and/or at least one information transfer process. The shot may be started by at least one triggering signal, e.g. a triggering signal provided by the computer 180. The shot may start by opening the shutter and the shot may be finished by closing the shutter. The image 117, most preferably comprising the side view image 152 and/or the top view image 154, may be taken by using the detector 116 during one shot of the detector 116. The top view image 154 may be taken directly and the side view image 152 may be taken by using the deflection device, e.g. the mirror. The deflection device 124 and/or the detector 116 may be adapted to be moved between the plurality of plant specimens 114 and/or the single plant specimen 120 and/or the group of plant specimens 122 specimens and/or between and/or over the plant container 126, e.g. by using at least a part of the motion system 162. In general, the screening device 110 may comprise more than one deflection device 124 and/or more than one detector 116 and/or more than one selection device 118.

The screening device 110 may further be adapted to perform a method for screening at least one plant specimen 112 in the plurality of plant specimens 114, preferably by using the screening device 110, as shown in FIG. 1A and described above. In the method for screening at least one plant specimen 112, the selection device 118 selects a single plant specimen 120 or a group of plant specimens 122 from the plurality of plant specimens 114 for imaging by the detector 116, wherein the selection device 118 may be constructed as described above.

The screening device 110 may further be adapted for performing a tracking method for tracking growth conditions of a plurality of plant specimens 114, wherein a plurality of plant specimens 114 are growing in growing medium 156 in at least one plant container 126, alternatively, a plurality of plant containers 126 comprise at least one plant specimen 112 growing in growing medium 156, preferably a tray as shown in FIG. 1A and FIG. 1B and in particular in FIG. 1C. The method is used for screening plant specimens 112, wherein at least one growth parameter is derived from the images 117, preferably for each single plant specimen 120 or for a group of plant specimens 122. The growth parameter may be stored in the database 182, preferably as a function of time and/or as a function of the single plant specimen 120 or a group of plant specimens 122 and/or as a function of the row 128 and/or as a function of the plant container 126. E.g., biometric data may be collected on each single plant specimen 120 or on each group of plant specimens 122, preferably on each seedling, and may be linked to a position of the single plant specimen 120 or the group of plant specimens 122 and/or the plant container 126 and/or the position of the seedling and/or the position on the plant container 126, preferably on the tray, such that the biometric data may be used to trigger decisions on any further action taken on the single plant specimen 120 or the group of plant specimens 122, preferably on an individual seedling. The further action may be e.g. a removal or transplantation to another plant container 126 and/or a sampling for analysis. Other actions may be possible.

Further, the tracking method may comprise the performance of a drought test and/or drought condition test and/or a water use efficiency test. Within the drought test and/or drought condition test and/or the water use efficiency test a variety of plant specimens 112 may be subjected to a lack or reduced amount of water over a period of time, wherein the plant specimens' 112 reaction to the lack of water may be recorded and/or monitored, preferably recorded on the database 182. A drought resistance and/or water use efficiency of the plant specimens 112 may be recorded and/or monitored. In an alternative example, the tracking method may comprise the performance of a nutrient efficiency test, a cold or heat stress test, salty water stress test, or combinations thereof.

The screening device 110 may further be adapted to support and/or perform a method for breeding plant specimens 112. The method comprises the steps of growing a plurality of plant specimens 114 of at least one species, preferably a grass-like species, e.g. rice, in at least one plant container 126. The plant specimens 112 are successfully transported to and from a screening station 166 by a motion system 162. The screening station 166 comprises the detector 116, wherein at least two images 117 of the plant specimens 112 from at least two different perspectives, e.g. a first perspective 148 and a second perspective 144, are acquired simultaneously by using the detector 116. At least one growth parameter of the plant specimens 112 in the screening station 166 is derived from the images 117. The method for breeding plant specimens 112 may comprise charging the at least one plant container 126 with growing medium 156 of uniform characteristics. A single plant specimen 120 or a plurality of plant specimens 114, preferably seeds, may be germinated in appropriate conditions, for a certain time period, allowing them to develop their erect structure.

Further, the single plant specimen 120 or the plurality of plant specimens 114 may grow in an environment of controlled climatic conditions, with controlled supply of liquid and/or with changing the positions of the plant specimen 112 within the environment as required to ensure at least substantially uniform exposure of all plant specimens 112, preferably all pluralities of plant specimens 114, to conditions in the environment. The method further may comprise the step of selecting plant specimens 112 for further breeding of a commercial use by comparing phenotypic characteristics of the plant specimens 112.

Further, the screening device 110 may be adapted and/or used to perform a use of the screening device 110 in a method for improved growing of plant specimens 112 for phenotyping, for selecting the most desired genotypes based on phenotype scoring. The method uses the screening device 110 according to the present invention, as described above. The method comprises: successively transporting the plant specimens 112 to and from a screening station 166 by a motion system 162, wherein the screening station 166 comprises the detector 116, wherein at least one image 117 of the plant specimens 112 from at least one perspective 148 is acquired by using the detector 116, preferably at least two images 117 of the plant specimens 112 from at least two different perspectives 144, 148 are acquired simultaneously by using the detector 116, wherein at least one growth parameter of the plant specimens 112 in the screening station 166 is derived from the image(s) 117.

The method for improved growing of plant specimens for phenotyping further may comprise displacing the plant specimens 112 automatically during their growing cycle so as to avoid extended exposure to a particular microenvironment.

The screening device 110 may further be adapted for performing a method for rapid analysis of stress resistance of growing plant specimens 112. The method uses the screening device 110 according to the present invention. The method comprises: growing the plant specimens 112 under stress conditions; successfully transporting the plant specimens 112 to and from a screening station 166 by a motion system 162, wherein the screening station 166 comprises the detector 116, wherein at least an image 117 of the plant specimens 112 from at least one perspective 148 is acquired, preferably at least two images 117 of the plant specimens 112 from at least two different perspectives 144, 148 are acquired simultaneously by using the detector 116, preferably a first perspective 148 and a second perspective 144, are acquired simultaneously by using the detector 116, wherein at least one growth parameter of the plant specimens 112 in the screening station 166 is derived from the images 117; and analyzing the stress resistance of the plant specimens 112 based on a growth parameter.

If a biotic and/or an abiotic treatment may be applied to the plant specimens 112, the effect of this treatment on e.g. plant growth may be assessed in an automated way. For example, an effect of fungi and/or fungicides and/or insects and/or insecticides and/or temperature treatments and/or chemicals and/or light and/or nutritional levels or other stress factors may be analyzed. The impact of the mentioned or not mentioned effects may be investigated with high accuracy at the level of single plant specimens 120 or a group of plant specimens 122, preferably of individual seedlings.

FIG. 1B shows a part of a screening device 110 according to the present invention, in particular a camera setup which may comprise the detector 116 and a deflection device 124, preferably a mirror 136. The deflection device 124, preferably the mirror 136 e.g. located between rows 128 of plant specimens 112, may be tilted, preferably by an angle of a, as shown in FIG. 1B. Further, the shielding element 158, preferably a black background 160, is shown. The shielding element 158 may be used to block e.g. unwanted objects and/or reflected views.

FIG. 1C shows a picture of a plant container 126, preferably designed as a tray setup, with rows 128, preferably 5 rows 128, of plant specimens 112. Each row 128 may be identified by identifiers 176, preferably by row identifiers 176 and/or barcodes and/or RFIDs.

FIGS. 1A, 1B and 1C shows an exemplary use of the present invention, wherein the side view image 152 is taken by the top view camera 138 by use of the deflection device 124. The side view image 152 is used for making phenotypic measurements. The top view camera 138 and one deflection device 124, a single mirror 136, are adapted for selecting the single plant specimen 120 or the group of plant specimens 122 from the plurality of plant specimens 114. The selection device 118 comprises the deflection device 124, the single mirror 136. The deflection device 124 is adapted for being used to take the side view image 152 by imaging the plant specimens 112. Thus, only the top view camera 138 and the deflection device 124 is used for making the selection. The side view image 152 is generated by collecting electromagnetic waves, e.g. light, being emitted and/or reflected from a side of the single plant specimen 120 or the group of plant specimens 122 by using the deflection device 124, the single mirror 136, and the detector 110. The deflection device 124 and/or the detector 116 are adapted to be moved between the plurality of plant specimens 114 and/or the single plant specimen 120 and/or the group of plant specimens 122 specimens and/or between and/or over the plant container 126 by using at least a part of the motion system 162.

Further, FIGS. 1A, 1B and 1C shows a further exemplary use of the present invention, wherein in addition to the example described above, the camera 129 also takes a top view image 154 next to the side view image 152. In this example, the screening device 110 is adapted for being used to take the side view image 152 and the top view image 154, e.g. simultaneously, by using one and the same detector 116 and one deflection device 124, thus, one mirror 136. The top view image 154 is generated by collecting electromagnetic waves, e.g. light, being emitted and/or reflected from the single plant specimen 120 or the group of plant specimens 122 directly, by using the detector 110, and not by using the deflection device 124. The two images 117 are captured by one single shot of the detector 116, e.g. by one single shot of the camera 129. The two images 117 appear on the detector 116 and/or on the sensor chip 132, e.g. next to each other. The output of the screening device 110 may comprise the top view image 154 and/or the side view image 152. The output of the screening device 110 comprises the electromagnetic waves generating the images 117, e.g. the top view image 154 and/or the side view image 152. The screening device 110 is adapted for acquiring more than one spatially resolved image 117, e.g. from different perspectives, e.g. the side view image 152 and the top view image 154, by only one shot of the detector 116, preferably simultaneously. The shot of the detector 116 is an event of the detector 116 and/or a step in a method of acquiring the images 117 by the detector 116. The image 117, comprising e.g. the side view image 152 and the top view image 154, is taken by using the detector 116 during one shot of the detector 116. The top view image 154 is taken directly and the side view image 152 is taken by using the deflection device 124.

LIST OF REFERENCE NUMBERS

| | |
|---|---|
| 110 | screening device |
| 112 | plant specimen |
| 114 | plurality of plant specimens |
| 116 | detector |
| 117 | image |
| 118 | selection device |
| 120 | single plant specimen |
| 122 | group of plant specimens |
| 124 | deflection device |
| 126 | plant container |
| 128 | row |
| 129 | camera |
| 130 | image-sensitive detector element |
| 132 | sensor chip |
| 134 | optical element |
| 136 | mirror |
| 138 | top view camera |
| 140 | arrows |
| 146 | first image |
| 148 | first perspective |
| 142 | second image |
| 144 | second perspective |
| 150 | direct view |
| 152 | side view image |
| 154 | top view image |
| 156 | growing medium |
| 158 | shielding element |
| 160 | background |
| 162 | motion system |
| 164 | motion stage |
| 166 | screening station |
| 168 | transport direction |
| 170 | imaging direction |
| 172 | reflective surface |
| 174 | reader |
| 176 | identifier |
| 178 | image analysis device |
| 180 | computer |
| 182 | database |
| 184 | finger camera |
| 186 | housing |

The invention claimed is:

1. A screening device for screening at least one plant specimen in a plurality of plant specimens, comprising a detector adapted for acquiring spatially resolved images and at least one selection device adapted for selecting a single plant specimen or a group of plant specimens from the plurality of plant specimens for imaging by the detector, wherein said selection device comprises a deflection device adapted for deflecting electromagnetic waves propagating between the plant specimens and the detector, and wherein said screening device further comprises at least one plant container containing a plurality of plant specimens or a plurality of plant containers containing at least one plant specimen.

2. The screening device of claim 1, wherein the screening device is adapted to create at least one side view image by using the deflection device.

3. The screening device of claim 1, wherein the screening device is adapted to simultaneously acquire at least two images of a single plant specimen or of a group of plant specimens from at least two different perspectives by using the detector.

4. The screening device of claim 1, wherein the screening device comprises at least one shielding element adapted to create a background for at least one of the images.

5. The screening device of claim 1, wherein the screening device comprises at least one reader adapted to read at least one information from at least one identifier assigned to a single plant specimen or to a group of plant specimens.

6. The screening device of claim 5, wherein the at least one identifier is at least one contactless identifier.

7. The screening device of claim 6, wherein the at least one contactless identifier is at least one contactless electronic identifier.

8. The screening device of claim 7, wherein the at least one contactless electronic identifier is at least one RFID.

9. The screening device of claim 1, wherein the screening device comprises at least one image analysis device adapted to perform at least one image analysis of at least one of the images.

10. The screening device of claim 9, wherein the image analysis device is adapted to generate at least one growth parameter of the single plant specimen or the group of plant specimens.

11. The screening device of claim 1, further comprising at least one database for recording data regarding the plant specimens.

12. The screening device of claim 11, wherein the data regarding the plant specimens is at least one of the following: at least one image of the single plant specimen or of the group of plant specimens; at least one growth parameter derived from at least one image of the single plant specimen or of the group of plant specimens; information from at least one identifier.

13. The screening device of claim 1, wherein the screening device is adapted to repeatedly acquire images of each single plant specimen or of each group of plant specimens.

14. The screening device of claim 13, wherein the screening device is adapted to repeatedly acquire images of each single plant specimen or of each group of plant specimens with a time delay in between each acquiring.

15. A method for improved growing of plant specimens for phenotyping or for selecting the most desired genotypes based on phenotype scoring using the screening device of claim 1, wherein said method comprises:
(i) successively transporting the plant specimens to and from a screening station by a motion system, wherein the screening station comprises the detector, wherein at least one growth parameter of the plant specimens in the screening station is derived from the images; and
(ii) controlling at least one growth condition of the plant specimens.

16. A method for rapid analysis of stress resistance of growing plant specimens using the screening device of claim 1, wherein said method comprises:
(i) growing the plant specimens under stress conditions;
(ii) successively transporting the plant specimens to and from a screening station by a motion system, wherein the screening station comprises the detector, wherein at least one growth parameter of the plant specimens in the screening station is derived from the images; and
(iii) analyzing the stress resistance of the plant specimens based on the growth parameter.

17. The screening device of claim 1, wherein the plurality of plant containers contain the plant specimens growing in rows.

18. A method for screening at least one plant specimen in a plurality of plant specimens using the screening device according to claim 1.

19. A method for screening at least one plant specimen in a plurality of plant specimens using a screening device comprising a detector and at least one selection device, comprising:
   (a) selecting a single plant specimen or a group of plant specimens from a plurality of plant specimens for imaging using said selection device;
   (b) acquiring spatially resolved images of said single plant specimen or said group of plant specimens using said detector,
   wherein the selection device comprises one deflection device, wherein the deflection device deflects electromagnetic waves propagating between the plant specimens and the detector, and wherein the deflection device is used for said imaging by the detector.

20. A tracking method for tracking growth conditions of a plurality of plant specimens, wherein a plurality of plant specimens are growing in growing medium in at least one plant container or wherein a plurality of plant containers comprise at least one plant specimen growing in growing medium, wherein the method of claim 19 is used for screening the plant specimens, wherein at least one growth parameter is derived from the images, and wherein the growth parameter is stored in a database.

21. The tracking method of claim 20, wherein one or more of a drought test and a water use efficiency test is performed in which a variety of plant specimens is subjected to a lack or reduced amount of water over a period of time, wherein the plant specimens' reaction to the lack of water is recorded and monitored.

22. The tracking method of claim 20, wherein at least one growth parameter is derived from the images for each single plant specimen or group of plant specimens.

23. The tracking method of claim 20, wherein the growth parameter is stored in a database as one or more of: as a function of time; as a function of the single plant specimen or group of plant specimens; as a function of the row; as a function of a plant container.

24. The method of claim 19, wherein the plant specimen is a grass-like seedling.

* * * * *

UNITED STATES PATENT AND TRADEMARK OFFICE
CERTIFICATE OF CORRECTION

| | | |
|---|---|---|
| PATENT NO. | : 9,074,989 B2 | Page 1 of 1 |
| APPLICATION NO. | : 14/129449 | |
| DATED | : July 7, 2015 | |
| INVENTOR(S) | : Frederik Leyns et al. | |

It is certified that error appears in the above-identified patent and that said Letters Patent is hereby corrected as shown below:

On the Title Page:

Item (75), Inventors: "Cádric Vandaele, Wortegem-Petegem (BE)" should read

-- Cédrik Vandaele, Wortegem-Petegem (BE) --

Signed and Sealed this
Fifth Day of January, 2016

Michelle K. Lee
*Director of the United States Patent and Trademark Office*